United States Patent
Thor et al.

(10) Patent No.: US 11,969,417 B2
(45) Date of Patent: Apr. 30, 2024

(54) TOPICAL FORMULATION FOR USE IN ALOPECIA

(71) Applicant: TOMORROWLABS GMBH, Vienna (AT)

(72) Inventors: Dominik Thor, Vienna (AT); Dominik Duscher, Linz (AT)

(73) Assignee: TOMORROWLABS GMBH, Vienna (AT)

( * ) Notice: Subject to any disclaimer, the term of this patent is extended or adjusted under 35 U.S.C. 154(b) by 204 days.

(21) Appl. No.: 17/419,915

(22) PCT Filed: Jan. 28, 2020

(86) PCT No.: PCT/EP2020/052046
§ 371 (c)(1),
(2) Date: Jun. 30, 2021

(87) PCT Pub. No.: WO2020/157064
PCT Pub. Date: Aug. 6, 2020

(65) Prior Publication Data
US 2022/0062251 A1    Mar. 3, 2022

Related U.S. Application Data

(60) Provisional application No. 62/797,387, filed on Jan. 28, 2019.

(30) Foreign Application Priority Data

Nov. 21, 2019 (EP) .................................. 19210779

(51) Int. Cl.
| | |
|---|---|
| A61K 31/4412 | (2006.01) |
| A61K 9/00 | (2006.01) |
| A61K 31/16 | (2006.01) |
| A61K 31/191 | (2006.01) |
| A61K 31/4196 | (2006.01) |
| A61K 31/444 | (2006.01) |
| A61P 17/14 | (2006.01) |

(52) U.S. Cl.
CPC ........ *A61K 31/4412* (2013.01); *A61K 9/0014* (2013.01); *A61K 31/16* (2013.01); *A61K 31/191* (2013.01); *A61K 31/4196* (2013.01); *A61K 31/444* (2013.01); *A61P 17/14* (2018.01)

(58) Field of Classification Search
CPC .................................................. A61K 31/4412
See application file for complete search history.

(56) References Cited

U.S. PATENT DOCUMENTS

| | | | |
|---|---|---|---|
| 10,016,347 B2 | 7/2018 | Ishmael | |
| 2010/0092546 A1 | 4/2010 | Gurtner et al. | |
| 2010/0172865 A1* | 7/2010 | Shantha | A61K 31/506 |
| 2012/0003300 A1 | 1/2012 | Isaacs et al. | |
| 2017/0312206 A1* | 11/2017 | Davis | A61K 8/4933 |

FOREIGN PATENT DOCUMENTS

| | | |
|---|---|---|
| EP | 3195854 | 7/2017 |
| FR | 2854243 | 10/2004 |
| WO | WO 2020/061474 | 3/2020 |

OTHER PUBLICATIONS

Flagg et al., "Screening shelating inhibitors of HIF-proly hydroxylase domain 2 (PHD2) and factor inhibiting HIF (FIH)", Journal of Inorganic Biochemistry, Elsevier Inc, US vol. 113, Mar. 9, 2012, pp. 25-30 (Year: 2012).*

"Top 10 Myths About Hair Transplants", Midland Skin, Oct. 3, 2016 (Year: 2016).*

Matsuzaki et al., "Role of hair papilla cells on induction and regeneration processes hair follicles", Wound Repair Regen., Nov. 1998 (Year: 1998).*

Shannon C Flagg et al, "Screening chelating inhibitors of HIF-proly hydroxylase domain 2 (PHD2) and factor inhibiting HIF (FIH)", Journal of Inorganic Biochemistry, Elsevier Inc, US, vol. 113, Mar. 9, 2012, pp. 25-30.

* cited by examiner

*Primary Examiner* — John S Kenyon
*Assistant Examiner* — Gillian A Hutter
(74) *Attorney, Agent, or Firm* — McDonnell Boehnen Hulbert & Berghoff LLP

(57) ABSTRACT

The invention relates to a composition comprising a HIF-1a activity potentiating agent for use in a method of preventing or treating hair loss, wherein the HIF-1a activity potentiating agent is an iron chelator, preferably Deferiprone. The invention further relates to a composition for topical application, comprising a HIF-1a activity potentiating agent that is an iron chelator. Furthermore, the invention relates to a method for cosmetic treatment or prevention of hair loss, comprising topical application of a composition comprising a HIF-1a activity potentiating agent that is an iron chelator to an area of skin.

15 Claims, 3 Drawing Sheets

Fig. 2 B, C
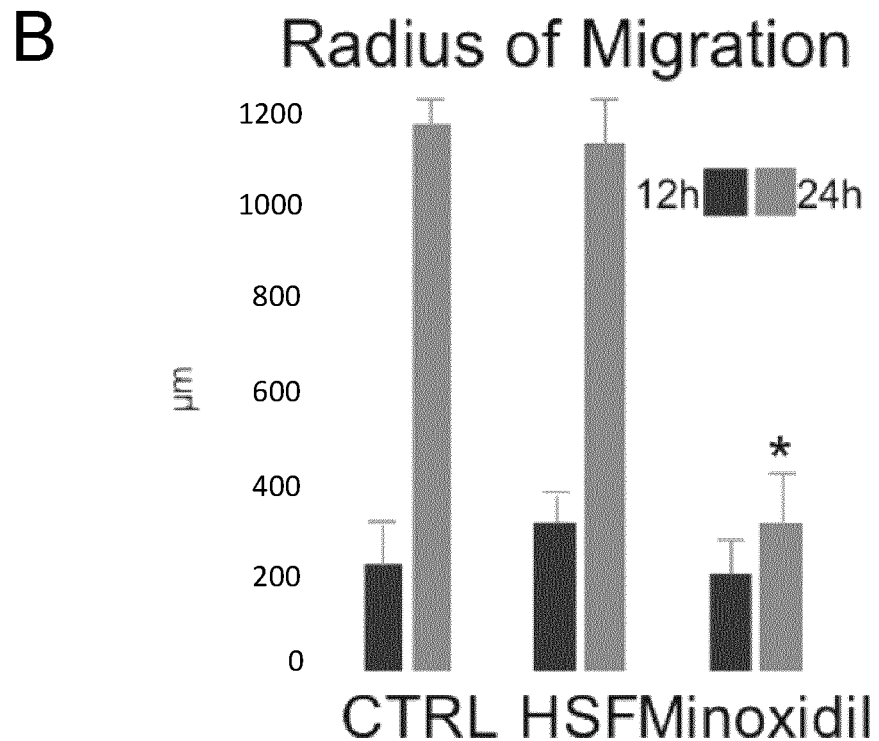
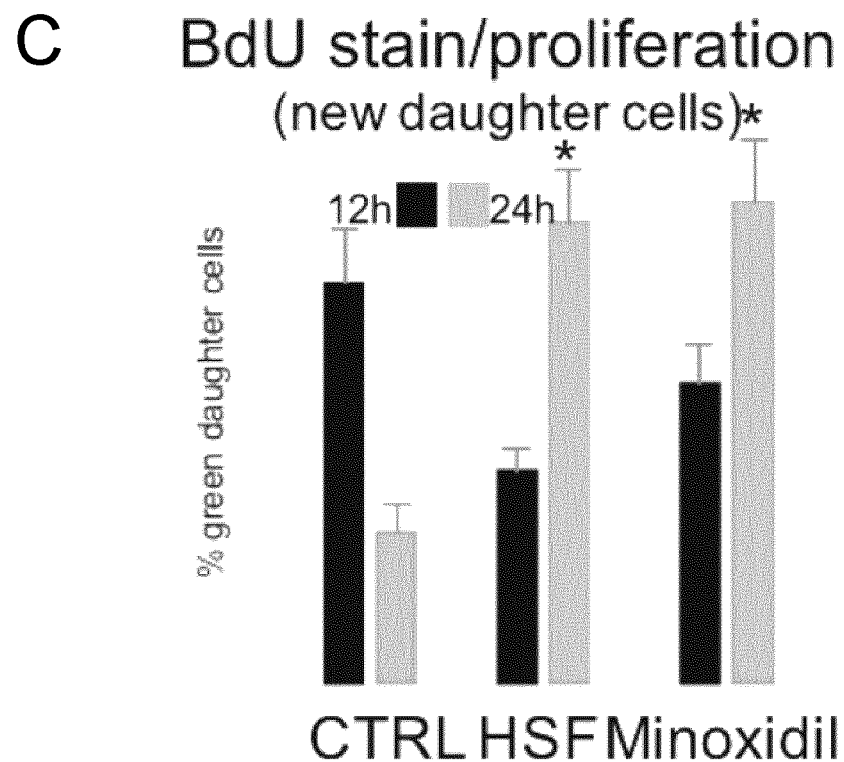

TOPICAL FORMULATION FOR USE IN ALOPECIA

CROSS REFERENCE TO RELATED APPLICATION

This patent application is a U.S. national phase of International Application No. PCT/EP2020/052046 filed on Jan. 28, 2020, which claims the benefit and priority of U.S. Application No. 62/797,387, filed Jan. 28, 2018 and EP Patent Application No. 19210779.5, filed on Nov. 21, 2019, the disclosures of which are incorporated by reference herein in their entirety.

The present invention relates to novel compositions for preventing or treating hair loss comprising a HIF-1α activity potentiating agent that is an iron chelator. The invention also relates to a method for cosmetic treatment or prevention of hair loss, comprising topical application of the composition to an area of skin.

BACKGROUND OF THE INVENTION

Hair is regarded as one of the characteristic feature of mammals and serves a number of different functions which include protection against external factors, production of sebum, apocrine sweat and pheromones, impact on social and sexual interactions, thermoregulation and provision of a resource for stem cells. Essentially a mini-organ, a hair follicle (HF) has a complex but well-organized structure, differentiating from hair follicle stem and progenitor cells. During embryonic development, the formation of HF is primarily regulated by mesenchymal-epithelial interactions within the dermal papilla niche. These interactions remain responsible for the postnatal hair growth and regeneration cycle. Dermal papilla cells are the main components of the mesenchymal compartments in hair bulb, serving an instructional role by generating signals to regulate the behaviour of neighbouring epithelial cells during the hair cycle. These epithelial cell signalling pathways govern the dermal papilla and thereby hair growth and maintenance. Hair growth is a continuous cyclic process and all mature follicles go through a growth cycle consisting of four main phases; growth (anagen), regression (catagen), rest (telogen), and shedding (exogen). The duration of each phase varies based on the location of the hair, nutritional and hormonal status, and age.

Hair loss is a common problem, experienced by men and women of all ages. The most common cause of hair loss is male-pattern hair loss (MPHL) and female pattern hair loss (FPHL), which is hair loss that primarily affects the top and front of the scalp. In males, MPHL hair loss often presents as a receding and often begins above the temples and vertex of the scalp. As it progresses, a rim of hair at the sides and rear of the head remains. Pattern hair loss by the age of 50 affects about half of males and a quarter of females.

The development of male pattern hair loss has been shown to be a result of a combination of genetics and the metabolite of the male hormone testosterone, dihydrotestosterone (DHT). DHT is produced systemically and if a genetic predisposition exists, 5alpha-reductase transforms testosterone to DHT in the affected hair follicles, which then results in a continuous shortening of hair growth (anagen) phases and prolongation of longer telogen phases, which leads to the shrinking of the hair follicle and ultimately causes hair growth to cease.

Alternative substances for the treatment of hair loss exist, with caffeine being used regularly in shampoos and tonic formulations. Caffeine has been argued to increase cAMP levels and promote cellular proliferation, which might to some degree counteract DHT-induced miniaturization of the hair follicle. The results of anti-hair loss treatments using caffeine are however unsatisfactory and more potent pharmaceutical solutions are currently the best available solution. As of today, the FDA has approved only two drugs, namely oral finasteride and topical minoxidil, for the effective treatment of this most common form of hair loss.

While finasteride has been associated with adverse effects such as inferior sexual function, topical Minoxidil is a popular, well tolerated topic drug with a favourable risk profile. However, it has to be continuously applied twice daily to counter hair loss and until recently its mechanism of action has not been well understood.

Recently however it has been shown that hair follicle development is dependent on perfectly coordinated principles of tissue regeneration, and the control of cell growth and migration, which closely relates it to wound healing. A main response to injury pathway, the Hypoxia Inducible Factor 1a (HIF-1α) regulatory pathway, has been identified as pivotal both in tissue regeneration and hair growth. HIF-1α signaling is significantly involved in tissue homeostasis and neovascularization resulting in the production of new collagen, elastin and nourishing blood vessel. It was shown that human HF stem/progenitor cells are reactive to hypoxia and modulating the functionality of the HIF pathway has been demonstrated to significantly enhance both tissue regeneration and hair growth.

Minoxidil topically applied to the scalp activates the angiogenic HIF-1-VEGF axis, demonstrating a potential positive pharmacologic effect for hair growth by inhibiting the HIF degrading enzyme prolylhydroxylase (PHD). It was suggested that by inhibiting PHD, Minoxidil prevents the hydroxylation of cellular HIF-1α, which then leads to degradation and HIF inactivation. This explains why the drug has to be applied twice daily. PHD inhibition only works if there is a constant supply of Minoxidil available to the cell. If a patient stops the treatment, hair loss will reoccur immediately.

Current efforts have failed to produce a technical solution that can counter the problem of pattern hair loss in a proven, effective, side-effect free and long lasting way.

A surgical solution to counter hair loss is a hair transplant. Today follicular unit transplantation (FUT) where a patient's hair is transplanted in naturally occurring groups of 1 to 4 hairs, called follicular units, has become the most common restoration procedure. Follicular units also contain sebaceous (oil) glands, nerves, a small muscle, and occasional fine vellus hairs. In follicular unit transplantation, these small units allow the surgeon to safely transplant thousands of grafts in a single session, which maximizes the cosmetic impact of the procedure.

Post-treatment after the FUT hair restoration procedure is an important part of the therapy, which ensures optimal outcomes. Doctors recommend that the patient avoids touching the swelling that will inevitably occur in the scalp area, avoids direct contact with UV rays and any form of strenuous activity, which could lead to excessive sweating, to ensure that the follicles have time to grow in properly and the skin can heal.

After undergoing an FUT procedure it is common for some patients to experience shedding of some newly transplanted hair grafts. Called 'shock hair loss' the follicular units may have been traumatized by transplantation and may react by shedding the hair. Most times the hair will regrow as the hair follicle remains healthy and just entered the rest (telogen) phase. There are cases however, when the shedding has been permanent.

Current efforts have failed to produce cosmetic or pharmaceutical preparations that can support the faster healing of the skin in the hair transplant area, minimizes the risk of 'shock hair loss' and helps the hair regrow.

The inventors have discovered that HIF-1α activity potentiating agents, which are iron chelators have a pronounced and long lasting effect on HIF-1α activity. Based on this observation, the present inventors have overcome one or more of the above stated problems of the prior art. Thus, the compositions of the present invention provide inter alia one or more of the following advantages: (i) the compositions have to be applied less often, (ii) the compositions have to be applied in smaller amounts, (iii) the compositions have an increased potency in supporting the growth of hair, (iv) the compositions show reduced side effects, (v) the compositions are better tolerated by the skin, (vi) the compositions support the healing of hair transplants, (vii) the compositions avoid shedding, (ix) the compositions clean, nourish, strengthen and/or repair the hair, (x) the compositions do not weigh down the hair.

SUMMARY OF THE INVENTION

In a first aspect, the present invention relates to a composition comprising a HIF-1α activity potentiating agent for use in a method of preventing or treating hair loss, wherein the HIF-1α activity potentiating agent is an iron chelator.

In a second aspect, the present invention relates to a composition for topical application comprising a HIF-1α activity potentiating agent that is an iron chelator.

In a third aspect, the present invention relates to a method for cosmetic treatment or prevention of hair loss, comprising topical application of a composition to an area of skin, wherein the composition comprises a HIF-1α activity potentiating agent that is an iron chelator.

DETAILED DESCRIPTION OF PREFERRED EMBODIMENTS

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention, which will be limited only by the appended claims. Unless defined otherwise, all technical and scientific terms used herein have the same meanings as commonly understood by one of ordinary skill in the art.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. As used in this specification and the appended claims, the singular forms "a", "an", and "the" include plural referents, unless the content clearly dictates otherwise.

The term "alopecia" as used within the context of the present specification refers to different forms of hair loss with varying underlying causes.

The term "pattern hair loss" as used within the context of the present specification includes male and female pattern hair loss and refers to a hair loss that affects primarily the top and front of the scalp.

The term "hair loss" as used within the context of the present specification may refer to a decrease in the number of active hair follicles, a shortening of the anagen phase, a prolongation of the catagen and/or telogen phase, and/or shrinking of individual hair follicles.

The term "HIF-1α activity potentiating agent" as used within the context of the present specification refers to a compound that increases HIF-1α activity. HIF-1α activity potentiating agents that exert their function by stabilizing HIF-1α are also called "HIF-1α stabilizing compounds". In most cases, stabilization of HIF-1α is achieved via inhibition of the HIF-1α degrading enzyme prolylhydroxylase (PHD).

The term "hypoxia mimetics" generally refers to HIF-1α activity potentiating agents. PHD uses $Fe^{2+}$ ions as a cofactor, and one way to inhibit PHD is by reducing the availability of $Fe^{2+}$ using iron chelators or by introducing metal ions like $Ni^{2+}$, $Mn^{2+}$ or $Co^{2+}$ that will compete with $Fe^{2+}$. The term "iron chelator" as used within the context of the present specification refers to a compound that binds $Fe^{2+}$ and thus reduces the amount of free $Fe^{2+}$ available for PHD mediated HIF hydroxylation reaction.

The term "Deferiprone" as used within the context of the present specification refers to 3-hydroxy-1,2-dimethylpyridin-4(1H)-one.

The term "thickening agent" as used within the context of the present specification refers to a compound that controls the viscosity of a formulation. Depending on the type of formulation, suitable thickening agents can be lipid thickening agents such as cetyl alcohol, stearyl alcohol, carnauba wax, and stearic acid; polymers that work by absorbing water, such as cellulose derivatives guar gum xanthan gum or gelatin; mineral thickening agents such as silica or bentonite; or synthetic thickening agents such as carbomer.

Hair follicle development and cycling is dependent on perfectly coordinated principles of tissue regeneration, and the control of cell growth and migration which closely relates it to wound healing. HIF-1α is a master transcription factor essential for neovascularization, tissue regeneration and wound healing. Minoxidil has been shown to have a short-lasting positive effect on hair loss due to inhibiting the HIF degrading enzyme PHD.

The present invention relates to the use of HIF-1α activity modulators that are iron chelators for increased hair growth and regeneration as part of compositions that can be applied by the patients. These compositions can include, but are not limited to, shampoos, conditioners, tonics and lotions.

In a first aspect, the present invention relates to a composition comprising a HIF-1α activity potentiating agent for use in a method of preventing or treating hair loss, wherein the HIF-1α activity potentiating agent is an iron chelator.

In studies employed in the present invention, it has unexpectedly been discovered that by topically applying HIF-1α activity modulators, which are iron chelators to the scalp of patients, hair follicle development is improved. In a 3D spheroid culture model, it was demonstrated that the iron chelator Deferiprone significantly increases dermal papilla cell (DP) cell proliferation without impeding DP cell migration (FIG. 2). In contrast, treatment with Minoxidil resulted in a significant reduction of DP cell migration. The data indicate that the physiological properties of DP cells are impaired by treatment with Minoxidil, but not by treatment with Deferiprone.

Without wishing to be bound by theory, the advantageous effect of iron chelators compared to Minoxidil on dermal papilla cells may also be related to longer lasting prevention of HIF degradation which helps to prevent, stop and counter pattern hair loss and other forms of hair loss.

The HIF-1α activity modulators have been shown to prevent HIF degradation through the binding (and subsequent excretion) of cellular iron, an important co-factor in the hydroxylation of cellular HIF-1α, which normally leads to VHL-dependent proteasome degradation and thus inactivation of HIF and the signalling cascade. HIF-1α activity modulators ensure that HIF enters the nucleus of the hair cell before hydroxylation occurs and thereby positively influenced hair growth and regeneration.

The present invention differs from the HIF increasing effect of Minoxidil, as it does not inhibit PHD directly, but instead eliminates co-factors, in particular $Fe^{2+}$ in the PHD-induced degradation process. Without wishing to be bound by theory, this likely results in a significantly longer lasting effect than Minoxidil treatment as the effect continues until unbound iron levels recover on a cellular level. It has also further unexpectedly been discovered that applying HIF-1α activity modulators topically to the scalp of patients that have received hair transplants enhances the healing of the skin in the scalp area, helps to minimize shedding as a side effect of the treatment and supports the growth of the transplanted hair.

In studies linked to the present invention HIF-1α activity modulators have been shown to prevent HIF degradation, with contributes to the optimal healing of the skin and follicular units in the transplant thanks to beneficial effects on cell migration, cell survival, cell division, growth factor release, and matrix synthesis throughout the healing process.

Minoxidil is known to cause multiple side effects. In contrast, Deferiprone is associated with favourable effects on dermal quality and skin cell function when applied as a topical treatment to the skin. The stimulatory capacity for both hair and skin cells without adverse effects on the cellular and tissue level make Deferiprone a leading compound for aesthetic and regenerative applications.

In preferred embodiments of the composition for use according to the first aspect, the HIF-1α activity potentiating agent is selected from the group consisting of Deferiprone, Deferoxamine, sodium gluconate, 2,2'-dipyridyl, Deferasirox, and 3-hydroxy-4-oxo-1(4H)-pyridinealanine.

In preferred embodiments of the composition for use according to the first aspect, the HIF-1α activity potentiating agent is selected from the group consisting of Deferoxamine, Deferiprone and sodium gluconate. In preferred embodiments, the HIF-1α activity potentiating agent is selected from the group consisting of Deferoxamine and Deferiprone. In preferred embodiments, the HIF-1α activity potentiating agent is Deferiprone.

In preferred embodiments of the composition for use according to the first aspect, the composition comprises Deferiprone at a concentration of 0.001-5.0% w/v, particularly 0.005-2.0% w/v, more particularly 0.010-1.0% w/v. In preferred embodiments of the composition for use according to the first aspect, the composition comprises Deferiprone at a concentration of approximately 1.0% w/v.

In preferred embodiments of the composition for use according to the first aspect, the composition is suitable for topical application, in particular topical application to a human scalp.

In preferred embodiments of the composition for use according to the first aspect, the composition (a) supports the growth of hair; (b) supports the growth of transplanted hair; (c) supports the healing of a hair transplant, in particular by supporting the healing of transplanted skin and/or skin in the area surrounding a hair transplant; (d) avoids shedding of hair and/or (e) avoids shedding of transplanted hair, in particular by supporting the healing of transplanted follicular units.

In the context of the present specification, supporting the growth of hair refers to one or several of the following: increasing the number of active follicles, prolonging the anagen phase, shortening the catagen and/or telogen phase, preventing shrinking/miniaturization of the hair follicle.

The pronounced and long lasting effect on HIF-1α activity not only supports hair growth but also has a positive effect on tissue regeneration and wound healing. Thus, the composition for use according to the invention supports the healing of a hair transplant.

The composition for use according to the first aspect of the invention is especially useful in preventing or ameliorating pattern hair loss.

In preferred embodiments of the composition for use according to the first aspect, the composition has to be applied once a day. Due to the long lasting effect of the composition according to the present invention, the composition has to be applied less often than known compositions. This advantage is important for increasing patient compliance. It also reduces the side-effects associated with the multiple applications per day which are required when using known compositions. Another advantage of the composition for use according to the first aspect of the invention is that a smaller amount of the composition has to be applied compared to compositions known in the art.

Preferred embodiments of the composition are a shampoo, a conditioner, a tonic or a lotion, in particular a shampoo. In preferred embodiments of the composition for use according to the first aspect, the composition is a shampoo and additionally comprises a shampoo base comprising at least 50% of water, and an active detergent agent comprising an anionic, cationic, nonionic, and/or amphoteric or zwitterionic surfactant. In preferred embodiments, the shampoo base comprises at least 60% of water, more particularly 60-75% of water. In preferred embodiments, the active detergent agent comprises about 5-12 wt-%, particularly about 8-10 wt-% of an anionic surfactant. In preferred embodiments, the active detergent agent comprises about 1-10 wt-%, particularly about 0.5-5.0 wt-%, more particularly about 0.75-2.0 wt-% of a nonionic surfactant. In preferred embodiments, the active detergent agent comprises about 0.2-2.0 wt-%, particularly about 0.5-1.0 wt-% of a quaternary ammonium salt. In preferred embodiments, the active detergent agent comprises about 0.5-2.0 wt-% of an amphoteric or zwitterionic surfactant.

In preferred embodiments, the shampoo base has a viscosity of about 600 to 800 cps.

In preferred embodiments, the shampoo comprises a thickening agent.

A positive effect of the formulation of the shampoo is that it does not weigh down the hair.

The composition for use according to the first aspect of the invention has the additional advantage that the skin tolerates it better than known compositions. Compositions known in the art often comprise significant amounts of alcohol, which lead to irritation of the skin.

In a second aspect, the present invention relates to a composition for topical application, comprising an HIF-1α activity potentiating agent that is an iron chelator.

In preferred embodiments of the composition according to the second aspect, the HIF-1α activity potentiating agent is selected from the group consisting of Deferiprone, Deferoxamine, sodium gluconate, 2,2'-dipyridyl, Deferasirox, and 3-hydroxy-4-oxo-1 (4H)-pyridinealanine, in particular Deferoxamine, Deferiprone and sodium gluconate.

In preferred embodiments of the composition according to the second aspect, the HIF-1α activity potentiating agent is selected from the group consisting of Deferoxamine, Deferiprone and sodium gluconate. In preferred embodiments, the HIF-1α activity potentiating agent is selected from the group consisting of Deferoxamine and Deferiprone. In preferred embodiments, the HIF-1α activity potentiating agent is Deferiprone.

In preferred embodiments of the composition according to the second aspect, the composition comprises Deferiprone at a concentration of 0.001-5.0% w/v, particularly 0.005-2.0% w/v, more particularly 0.010-1.0% w/v.

In preferred embodiments, the composition is a shampoo, a conditioner, a tonic or a lotion.

In a third aspect, the present invention relates to a method for cosmetic treatment or prevention of hair loss, comprising topical application of a composition to an area of skin, in particular the scalp of a human, wherein the composition comprises a HIF-1α activity potentiating agent that is an iron chelator.

In preferred embodiments of the method according to the third aspect of the invention, the composition is the composition according to the second aspect of the invention.

In preferred embodiments of the method according to the third aspect of the invention, the composition (a) supports the growth of hair; (b) supports the growth of transplanted hair; (c) avoids shedding of hair; (d) avoids shedding of transplanted hair; and/or (e) cleans, nourishes, strengthens and/or repairs the hair.

In preferred embodiments of the method according to the third aspect of the invention, the composition has to be applied once a day.

In another aspect, the present invention relates to a method of treating or preventing hair loss, comprising topical application of a composition to an area of skin, wherein the composition comprises a HIF-1α activity potentiating agent that is an iron chelator. In preferred embodiments, the composition is the composition according to the second aspect of the invention. In preferred embodiments, the composition (a) supports the growth of hair; (b) supports the growth of transplanted hair; (c) avoids shedding of hair; (d) avoids shedding of transplanted hair; and/or (e) cleans, nourishes, strengthens and/or repairs the hair. In preferred embodiments, the composition has to be applied once a day.

In another aspect, the present invention relates to a use of a HIF-1α activity potentiating agent that is an iron chelator in the manufacture of a medicament for the treatment or prevention of hair loss. In preferred embodiments, the medicament is the composition according to the second aspect of the invention. In preferred embodiments, the medicament (a) supports the growth of hair; (b) supports the growth of transplanted hair; (c) avoids shedding of hair; (d) avoids shedding of transplanted hair; and/or (e) cleans, nourishes, strengthens and/or repairs the hair. In preferred embodiments, the medicament has to be applied once a day.

Compounds suitable as HIF-1α activity modulators, in particular as HIF-1α activity potentiating agent according to the present invention in the context of hair follicle regeneration are iron chelators such as Deferiprone (DFP), Deferoxamine (DFO), sodium gluconate, 2,2'-dipyridyl, Deferasirox (DFR), and 3-hydroxy-4-oxo-1(4H)-pyridinealanine (mimosine). Also of interest are iron competitors such as cobalt chloride ($CoCl_2$), or other factors that may mimic hypoxia, such as hydroxylase inhibitors, including, ciclopirox and dimethyloxallyl glycine (DMOG). Other HIF hydroxylase inhibitors are described herein, including but not limited to, oxoglutarates, heterocyclic carboxamides, phenanthrolines, hydroxamates, and heterocyclic carbonyl glycines (including, but not limited to, pyridine carboxamides, quinoline carboxamides, isoquinoline carboxamides, cinnoline carboxamides, beta-carboline carboxamides, including substituted quinoline-2-carboxamides and esters thereof; substituted isoquinoline-3-carboxamides and substituted arylsulfonylaminohydroxamic acids and the like. Compounds reported to stabilize HIF-1α also include [(3-hydroxy-6-isopropoxy-quinoline-2-carbonyl amino]-acetic acid, [3-hydroxy-pyridine-2-carbonyl amino]-acetic acid, [N-(1-chloro-4-hydroxy-isoquinoline 3-carbonyl)-amino]-acetic acid, [(7-bromo-4-hydroxyisoquinoline-3-carbonyl)-amino]-acetic acid, [(7-chloro-3 hydroxy-quinoline-2-carbonyl)-amino]-acetic acid, [(1 bromo-4-hydroxy-7-chloromethyl-isoquinoline-3 carbonyl)-amino]-acetic acid, [(1-bromo-4-hydroxy-7 phenoxy-isoquinoline-3-carbonyl)-amino]-acetic acid, [(1 chloro-4-hydroxy-7-phenoxy-isoquinoline-3-carbonyl)amino]-acetic acid, [(1-chloro-4-hydroxy-7 isoquinoline-3-carbonyl)-amino]-acetic acid, [(1-chloro-4 hydroxy-isoquinoline-3-carbonyl)-amino]-acetic acid, [(4 hydroxy-7-phenoxy-isoquinoline-3-carbonyl)-amino]-acetic acid, [(4-hydroxy-7-phenylsulfanyl isoquinoline-3 carbonyl)-amino]-acetic acid, [(4-hydroxy-6 phenylsulfanyl-isoquinoline-3-carbonyl)-amino]-acetic acid, 4-oxo-1,4-dihydro-[1,10]phenanthroline-3-carboxylic acid, 4-hydroxy-5-methoxy-[1,10]phenanthroline-3-carboxylicacidethylester, [(7-benzyloxy-1-chloro-4-hydroxy isoquinoline-3-carbonyl)-amino]-acetic acid methyl ester, and 3-{[4-(3,3-dibenzyl-ureido)-benzenesulfonyl]-[2-(4 methoxy-phenyl)-ethyl]-1-amino}-N-hydroxy-propionamide.

EXAMPLE SECTION

Example 1

Figure 1:
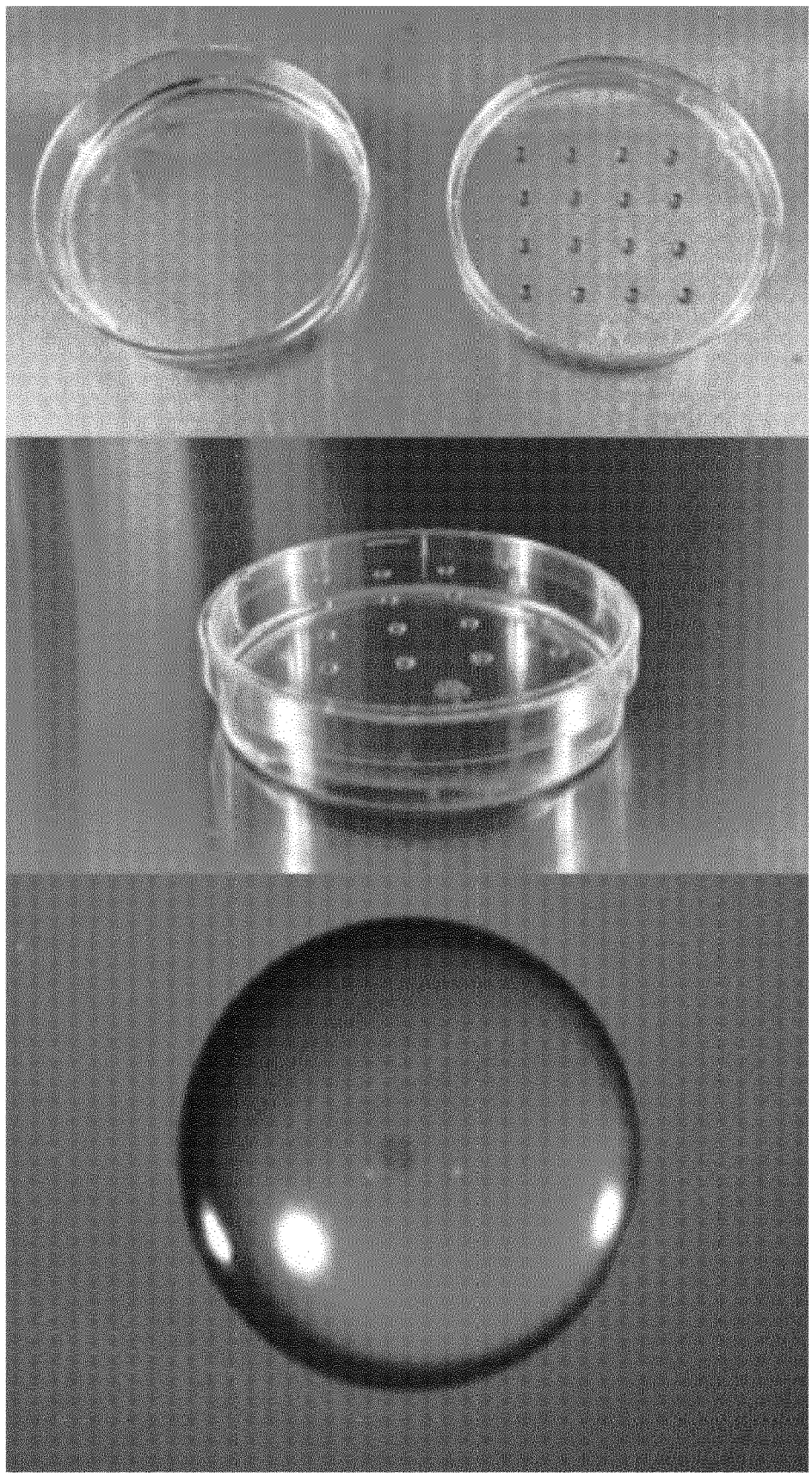
FIG. 1: 3D hanging drop culture of DPCs. The DPCs aggregate to stable spheroids over a period of 72 hours. After spheroid formation is complete, the samples are transferred into a 96 well plate for further cultivation and drug exposure.
Figure 2:
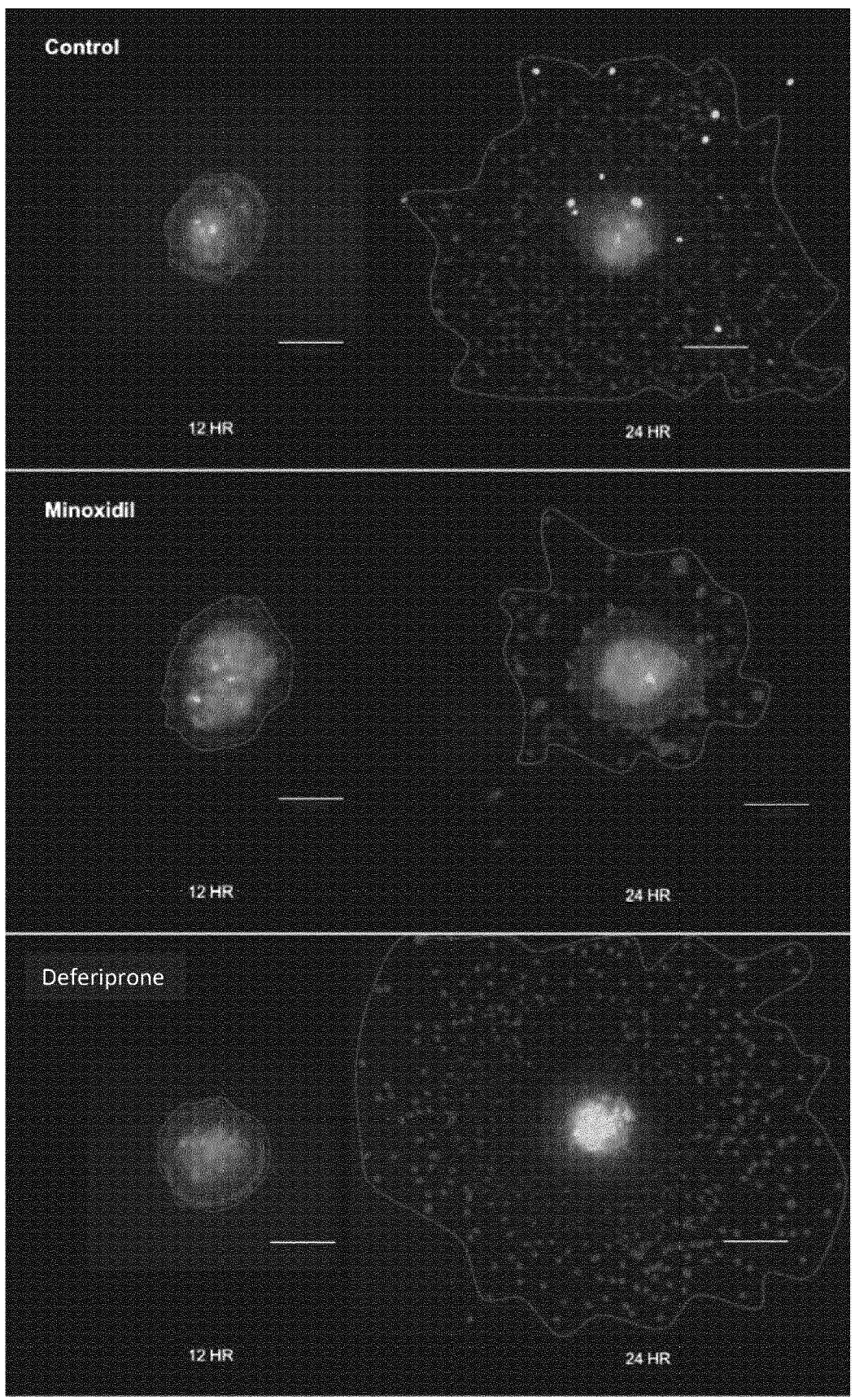
FIG. 2: Deferiprone significantly enhances DPC proliferation in a 3D spheroid culture model. (A) Representative images of spheroids stained for newly synthesized cells were taken after drug exposure for 12 hours (left column) and 24 hours (right column) respectively. Scale bars: 200 µm. (B) While Deferiprone treatment left the migratory activity of DPCs in culture unchanged, Minoxidil exposure resulted in a reduction of physiological cell motility demonstrated by a significantly reduced radius of migration around the spheroids after 24 hours. (C) Evaluating the synthesis of new daughter cells demonstrated a significantly enhanced proliferative activity for both Minoxidil and Deferiprone.

Preparation of a Topical Hair Tonic Composition

The present invention is illustrated by the following preparation of a topical hair tonic composition; to which it is of course not limited. The hair tonic is for the purpose of treating hair loss, improve hair quality and regeneration and the take rate after hair transplantation. A HIF-1α activity modulator for use herein is present in the hair tonic composition at a level of from 0.001% to 5% w/v, preferably from 0.005% to 2.0% w/v, more preferably 0.010% to 1.0% w/v.

In addition to the HIF-1α activity modulator, the hair tonic composition according to the present invention can contain ingredients conventionally used in hair tonic compositions. Examples of such optional ingredients are solvents such as purified water and ethanol; refrigerants such as menthol; humectants such as propylene glycol, glycerin and sorbitol; keratin-solubilizing agents such as lactic acid, resorcinol and salicylic acid; ethers such as polyoxyethylene oleyl ether and polyoxyethylene lauryl ether; vegetable oils such as olive oil and caster oil; higher alcohols such as cetyl alcohol and oleyl alcohol; hydrocarbons such as liquid paraffin and acetene; vitamin; perfumes; coloring agents; and preservatives. If necessary, ingredients for hair tonic preparations such as hormones, germicides, antiphlogistics, scalp-stimulating agents and the like can be incorporated in the hair tonic composition of the present invention. The hair tonic composition according to the present invention can be prepared in accordance with the general process for preparing an ordinary hair tonic composition except that the gibberellin and the optional proteolytic enzyme are incorporated therein.

Example 2

Preparation of a Shampoo Composition

The present invention is further illustrated by the following preparation of a shampoo composition; to which it is of course not limited. The shampoo is for the purpose of that is used for cleaning hair and also treating hair loss, improve hair quality and regeneration. A HIF-1α activity modulators for use herein is present in the shampoo composition at a level of from 0.001% to 5% w/v, preferably from 0.005% to 2.0% w/v, more preferably 0.010% to 1.0% w/v.

The shampoo base is a low viscosity solution which includes an anionic or nonionic surfactant. The viscosity of the shampoo base is preferably low enough such that additive ingredients are easily combined with the shampoo base. Typically the shampoo base has a viscosity from about 600 to 800 cps.

The shampoo base includes a mild detergent to effectively clean hair without damaging or stripping it. The low viscosity shampoo base is combined with a thickening agent and, optionally, one or more hair enhancing additives.

The shampoo base contains a major amount of water and is clear to opaque. As used herein, "a major amount of water" means that the shampoo base is made of no less than 50% water. Preferably the shampoo base contains about 60-75 wt-% water. The active detergent agent of the shampoo includes an anionic, nonionic, amphoteric or zwitterionic surfactant. A preferred detergent agent includes an anionic surfactant such as sodium lauroyl sarcosinate or N-lauroyl sarcosine. The shampoo base preferably contains about 5-12% wt-% anionic surfactant, more preferably about 8-10 wt-%.

The shampoo base can also include a specialized nonionic surfactant which can function as a foam stabilizer, viscosity control agent, or a conditioning agent. Where included, the shampoo base preferably contains about 0.5-5.0 wt-% nonionic surfactant, more preferably about 0.75-2.00 wt-%.

Useful nonionic surfactants include a carboxylic amide nonionic surfactant which is a condensation product of fatty acids and hydroxyalkyl amines, such as mono- and dialkanolamides of C8-C22 fatty acids. An example is mono- or di(C8-C22)alkanolamide. Commercially available, specialized nonionic surfactants suitable for use in the shampoo base include stearamide DEA, lauramide DEA, stearamide MEA, lauramide MEA, lauramide MIPA, myristamide MEA, myristamide MIPA, myristamide DEA, oleamide DEA, oleamide MEA, oleamide MIPA, cocamide DEA, cocamide MIPA, cocamide MEA, and other dialkanolamine and monoalkanolamine condensates.

Also useful are organic esters that function as nonionic surfactants and emollient esters. These include polyoxyethylene glycol (C7-C20) fatty acid, esters of glycerol, such as PEG-7 glyceryl cocoate, PEG-30 glyceryl cocoate, PEG-12 glyceryl laureate, and PEG-20 glyceryl oleate.

Another useful nonionic surfactant is a polyoxyethylene glycol (PEG) ether of the diester of methyl glucose and a fatty acid. Examples of such PEG compounds include PEG-120 methyl glucose dioleate, PEG-20 methyl glucose distearate, PEG-80 methyl glucose laureate, and PEG-20 methyl glucose sesquistearate.

The shampoo base can also include a cationic polymer, such as quaternary ammonium salt, to provide substantive conditioning, detangling and improved wet and dry compatibility. Examples of useful quaternary ammonium salts include polymeric quaternary ammonium salts, also referred to as "polyquaterniums" (i.e., -6, -7, -10, -11, -16), cetrimonium chloride and steartrimonium chloride. The shampoo base can include about 0.2-2.0 wt-%, preferably about 0.5-1.0 wt-%, of a quaternary ammonium salt.

Other additives can be included in the shampoo base in lesser, but effective, amounts. Useful additives include a chelating or sequestering agent such as disodium EDTA, tetrasodium EDTA, citric acid or lactic acid. A chelating or sequestering agent is typically added to stabilize the composition. Preferably about 0.001-0.75 wt-%, more preferably about 0.03-0.25 wt-%, is added to the shampoo base. Other additives include germicidal preservative agents such as methylchloroisothiazolinone, methylisothiazolinone, phenoxyethanol, esters of parabenzoic acid, diazolidinyl urea, and imidazolidinyl urea. Preferably, the preservative is added in an effective germicidal amount, typically about 0.05-1.25 wt-%. Other additives include an antioxidant such as ascorbic acid or BHA to inhibit deterioration, typically included at about 0.001-0.5 wt-%. An appropriate amount of natural or synthetic fragrance can also be added for aesthetic purposes. An opacifying agent such as glycol. Stearate or glycol distearate can be included at about 0.5-1.25 wt-% to give the shampoo an opaque or pearlescent appearance.

The shampoo base typically includes about 60-75 wt-% water, about 5-12 wt-% anionic surfactant, about 1-10 wt-% nonionic surfactant, about 0.2-2.0 wt-% of a quaternary ammonium salt and about 0.5-2.0 wt-% of an amphoteric or zwitterionic surfactant. Optionally, the shampoo base includes minor, but effective, amounts of a germicidal preservative agent, sequestering agent, antioxidant, or fragrance.

ITEMS

1. A composition for preventing or treating loss of hair on a scalp of a human being in the form of a shampoo, conditioner, tonic or lotion, comprising a suitable HIF-1α activity potentiating agent, such as an iron chelator, a hypoxia mimetic, a HIF hydroxylase inhibitors or HIF-1α stabilizing compound.

2. A composition for supporting the healing of hair transplants and the skin in the area of the transplant, avoid shedding as a side effect of the treatment and supporting the growth of the transplanted hair in the form of a shampoo, conditioner, tonic or lotion, comprising a suitable HIF-1α activity potentiating agent, such as an iron chelator, a hypoxia mimetic, a HIF hydroxylase inhibitors or HIF-1α stabilizing compound.

3. The composition of item 1 or 2, wherein the HIF-1α activity potentiating agent is present at a concentration of 0.1% to 50.0% volume/volume.

4. The composition of item 1 or 2, wherein the HIF-1α activity potentiating agent is Deferoxamine.

5. The composition of item 1 or 2, wherein the HIF-1α activity potentiating agent is Deferiprone.

6. The composition of item 1 or 2, wherein the HIF-1α activity potentiating agent is sodium gluconate.

7. A composition for preventing or treating loss of hair on a scalp of a human being according to item 1 or 2 or a kit comprising said composition for cosmetic applications such as such as cleaning, nourishing, strengthening and repairing the hair.

8. A composition for preventing or treating loss of hair on a scalp of a human being according to item 1 or 2 or a kit comprising said composition for use in therapy.

The invention claimed is:

1. A method for prevention of hair loss, comprising topically applying a composition comprising Deferiprone to an area of skin in a subject in need thereof, in an amount effective to prevent hair loss.

2. The method of claim 1, wherein the subject is a human subject, and wherein topical application comprises application to a scalp of the human subject.

3. The method of claim 1, wherein the method:
   a. supports growth of hair;
   b. supports growth of transplanted hair;
   c. supports healing of a hair transplant, by supporting the healing of transplanted skin and/or skin in the area surrounding a hair transplant;
   d. avoids shedding of hair; and/or
   e. avoids shedding of transplanted hair, by supporting the healing of transplanted follicular units.

4. The method of claim 1, wherein the composition is applied once a day.

5. The method of claim 1, wherein the composition is in the form of a shampoo, a conditioner, a tonic or a lotion.

6. A method for supporting hair growth, supporting healing of a hair transplant, and/or avoiding shedding of hair, comprising topically administering a composition comprising Deferiprone to a subject in need thereof, in an amount effective to support hair growth, support healing of a hair transplant, and/or avoid shedding of hair.

7. The method of claim 6, wherein the subject has received a hair transplant, and the method supports growth of transplanted hair, supports healing of transplanted hair, and/or avoids shedding of transplanted hair.

8. The method of claim 7 wherein the method supports healing of transplanted hair by supporting the healing of transplanted skin and/or skin in the area surrounding a hair transplant.

9. The method of claim 7 wherein the method avoids shedding of transplanted hair by supporting the healing of transplanted follicular units.

10. The method of claim 1, comprising Deferiprone at a concentration of 0.001-5.0% w/v.

11. The method of claim 1, comprising Deferiprone at a concentration of 0.005-2.0% w/v.

12. The method of claim 1, comprising Deferiprone at a concentration of 0.010-1% w/v.

13. The method of claim 6, comprising Deferiprone at a concentration of 0.001-5.0% w/v.

14. The method of claim 6, comprising Deferiprone at a concentration of 0.005-2.0% w/v.

15. The method of claim 6, comprising Deferiprone at a concentration of 0.010-1% w/v.

* * * * *